United States Patent [19]

Torrisi et al.

[11] Patent Number: 4,575,869
[45] Date of Patent: Mar. 11, 1986

[54] SAMPLE HOLDER WITH HANDLING SUPPORT FOR X-RAY SPECTROSCOPIC ANALYSIS

[75] Inventors: Angelo M. Torrisi, 10 Anpell Dr., Scarsdale, N.Y. 10583; Roland Urbano, Tuckahoe, N.Y.

[73] Assignee: Angelo M. Torrisi, Scarsdale, N.Y.

[21] Appl. No.: 611,047

[22] Filed: May 16, 1984

[51] Int. Cl.[4] .............................................. G01N 23/10
[52] U.S. Cl. ...................................... 378/47; 378/208; 356/246
[58] Field of Search ........................... 378/47, 208, 79; 356/246

[56] References Cited

U.S. PATENT DOCUMENTS 3,218,459 11/1965 Bens ........................................ 378/47
3,462,598 8/1969 Burke et al. ............................ 378/47
4,037,109 7/1977 Hosokawa et al. .................... 378/47
4,115,689 9/1978 Won ....................................... 378/47
4,448,311 5/1984 Houser ................................. 378/208

Primary Examiner—Alfred E. Smith
Assistant Examiner—T. N. Grigsby
Attorney, Agent, or Firm—Paul J. Sutton

[57] ABSTRACT

A disposable sample holder with a handling support for X-ray spectroscopic analysis of harmless or noxious powders, slurries, liquids, or gases, which includes a handling support for safe handling of the sample holder by either local or remote means. The handling support includes a stem extending from the surface of a cap or outer cover for the holder and a gripping member surmounting the stem. The handling support is designed for local tool handling by an operator or for remote handling by a controlled robot mechanism. Optionally, the handling support is provided with a septum through which a liquid, volatile, or gaseous sample material may be loaded into a closed sample holder by insertion of a hypodermic needle.

20 Claims, 22 Drawing Figures

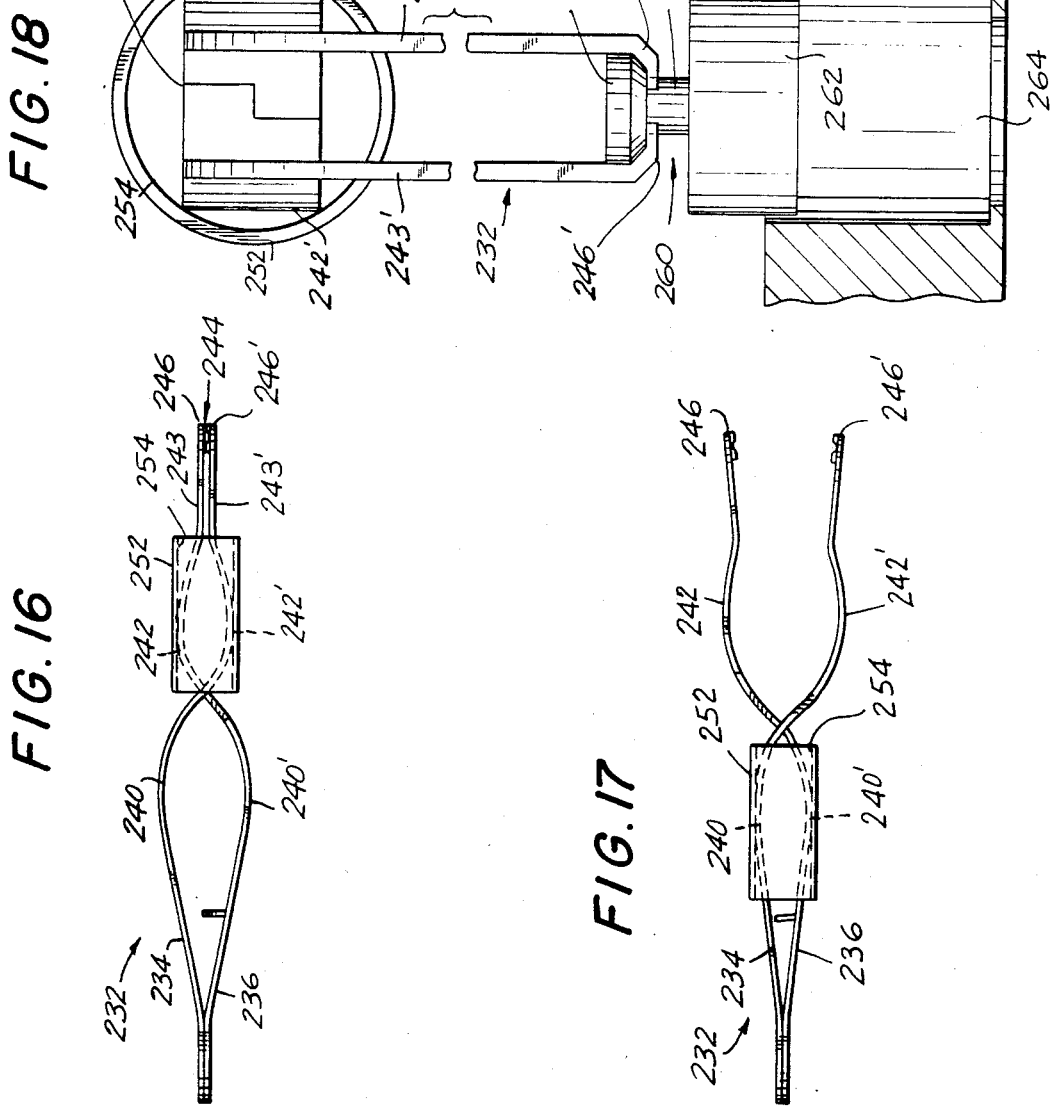

SAMPLE HOLDER WITH HANDLING SUPPORT FOR X-RAY SPECTROSCOPIC ANALYSIS

This invention relates generally to the field of disposable sample holders for X-ray spectroscopic analysis and more particularly to a handling support for a sample holder.

The field of spectroscopy involves the measurement of the spectra of certain material being analyzed. Without going into detail here, which is well-known to those familiar with the art, it can in summary be said that an atom releases a quantum of energy that emits a definite wave length of the electromagnetic spectrum where bombarded by X-rays. The spectroscope measures the energy or wavelength radiation emitted by a sample material and so verifies the qualitative or quantitative presence or absence of certain elements which generally are within a defined range associated with the sample being analyzed. The sample may be of any liquid, slurry, powder material, or industrial gases that can occur in the run of industry. Gasoline and oils are examples of liquid materials that are often analyzed when a suspected contaminate is the object of the analysis; the spectroscope may be a tool of the inorganic analysis of a sample such as a mineral ore powder.

The field of spectroscopy is that of high precision technology. The X-ray apparatus that is used to bombard the sample is finally dependent upon the quality of the presentation and preparation of the sample being analyzed, because a precise geometry of distance is involved in the measurement process.

A sample is positioned in a cylindrical sample holder that includes a holder body forming a cell adapted to contain the sample. A disposable sample holder is generally made of polyethylene or polypropylene and is generally intended to be disposed of after a single use. A sample holder will range in size between diameters of 20 to 57 mm and have a height of about 25 mm although this will vary.

The first phase of the analysis is in the preparation of the sample for spectroscopy. In one type of holder, a very thin plastic film is placed taut as an X-ray transparent window across the circular end face of the body of the holder and the skirt of the film is then secured to the outer wall of the body. The body is then inverted so that the window film face is positioned downwards. The holder cell is then filled with the sample through the top open face of the holder body. If the holder does not have an integral transverse wall, a cap is then placed on the top face to form a complete holder of a body with the cap. The sample holder is then placed in a cell positioner of the particular spectroscopic apparatus being used and the X-rays are applied to the downwardly positioned film face of the holder upon which the sample material is lying. The X-ray analysis may be conducted in an air, inert gas, or vacuum environment; if the sample material is to be analyzed in a vacuum, then the top wall, or cap side, of the sample holder must be vented so that the pressure in the cell does not cause the film to bulge across the lower face of the holder and so compromise the geometric precision of the measurement. Venting is accomplished in the type of sample holder being discussed by the placement of a vented cap that cooperates with structure in the body of the holder to pass air of the cell. In certain cases where air is to be replaced by another gas such as an inert gas, the same procedure is followed. Venting is made practical in the cases of high viscosity liquids and medium to high density powders by a baffle arrangement in the top wall or in the cap and holder that prevents these materials from escaping from the cell by creating a path that easily passes a gas but sets up an obstacle for the materials. The body of a holder that is being used in a venting process preferably forms a top well that can receive any overflow portion of the liquid sample that exudes through the baffled vent. In the case of a spectroscopic analysis of a sample that need not be vented, the top wall or top cap and the holder body preferably form a seal between them.

It is noted that there are spectroscopic analysis methods that involve a remote access X-ray where a liquid sample is impregnated into filter paper that in turn is placed between two film layers mounted on a cell holder that does not form a wall. The bottom of the body of the holder is configured for pressure positioning in the cell positioner of the spectroscopic apparatus.

When a sample is a noxious, contaminated, or caustic substance which should not be directly handled by a human, it is handled in two ways in the present state of the art. The holder can be handled locally by operator manipulation with a tool, as for example a tweezer, to grip the top of the holder or a clam shell gripping device to encircle the exterior of the sample holder. In other cases, a noxious sample is loaded into the cell of a holder in an isolation chamber in which the technician manipulates the holder with flexible gloves that extend into the chamber. Another type of isolation chamber procedure may include a loading station with a moving endless track to the spectroscope station where analysis is performed, and transit subsequently to either a waste disposal station or to a recovery station.

It is pointed out that often the sample material must be removed from the sample holder after analysis. Unloading of the sample may be required under various requirements, such as the sample being evidentiary in nature for a legal action, or the sample being valuable in itself, or the sample being a base reference that must be retained for future standards. Unloading of the sample is an added problem, especially for remote handling and even more so for robot handling.

A few observations can be made about a certain problem relating to the disposable sample holders now being used, namely, that of the lack of an efficient and safe handling device for operations of sample loading, or for placement or removal of sample holders in the cell positioner, or for sample unloading. First of all, even when the sample material is a non-noxious substance, such as oil or peroxide, spillage is to be avoided, for certain spilled materials can be unpleasant and often difficult to clean or may cause damage to the X-ray equipment. Second, handling noxious materials even by way of gloves extending into an isolation chamber cannot be said to be safe if spillage occurs. In fact, although the handling of noxious, unsafe, sample materials calls for robot remote precision handling mechanisms, such mechanisms have not been generally developed for the reason that the disposable sample holders as they now exist in the art are not adaptable to such robot handling. That is to say, the arms of a robot must be able to grasp the exterior of the sample holder which must then be positioned into a cell positioner, or the arms of a robot must be able to grasp the top of the body by tweezer, or able to grasp and snap on the cap onto the holder body subsequent to loading and to place the sample via the cap into the well of the cell positioner and finally, after analysis, reach into the well of the cell positioner, grasp the cap of the holder, and remove the holder from the well for sample disposal or recovery. Sample unloading adds further problems. All of the above must be done with precision and without spillage. The spectroscopic machines used today work from movable arrays of cell positioners each containing its own sample holder, so the task is not merely handling one sample holder but large numbers of them speedily, efficiently, and safely.

In prior art disposable sample holder devices known, robot handling is especially difficult. One type has an integral top wall with an extending toggle that can be used to break the top wall for venting after the sample materials have been loaded. The toggle, which is positioned at the bottom of a well, is difficult and insecure to grasp for handling purposes. Another cell holder device has a snap on cap with a tab that is used to pick up the holder, the holder forming no well. The cap is a snap-on type cap. In both cases, except for placement into and removal from a cell positioner, it is easier for a user to pick up the entire holder for manipulation purposes than to use either the toggle or the tab.

Remote handling, particularly remote robot precision handling, is especially difficult with present art devices.

The present invention contemplates a sample holder with a handling support for X-ray spectroscopic analysis that overcomes the limitations and disadvantages of the prior art by providing a sample holder with a handling support that meets the special needs of both immediate handling with a tool and remote precision handling of sample cell holders.

Accordingly, it is an object of the present invention to provide a sample holder with a handling support that allows precision handling access with a tool from a vantage point either at the top or at the side of the sample holder in preparation for spectrometric X-ray analysis.

It is a further object of the present invention to provide a sample holder with a handling support that allows safe and convenient loading of unstable or gaseous sample materials into disposable X-ray spectroscopic sample holders.

It is a further object of the present invention to provide a sample holder with a handling support that provides for both remote precision handling access and for convenient handling with a tool for hands-on preparation of the sample holder for spectrometric X-ray analysis.

It is yet another object of the present invention to provide a sample holder with a handling support that is positioned in a well of the holder so that the handling support can be grasped by a tool or by remote-controlled handling grips for preparation for spectroscopic X-ray analysis.

It is a further object of this invention to provide a sample holder with a handling support for a snap-on cap that is capable of being mounted onto the holder by the application of a remote-controlled handling apparatus.

It is a further object of this invention to provide a sample holder with a handling support for a cap for both hands-on and remote preparation of samples for spectroscopic X-ray analysis.

It is yet another object of this invention to provide a sample holder with a handling support on a cap that can be used for both hands-on and remote unloading of samples after spectroscopic X-ray analysis.

It is yet another object of the present invention to provide a sample holder with a handling support that is centrally mounted to the top wall of the holder and is accessible even by a tool handled by an operator or by a mechanism operated by a remotely controlled robot.

It is a further object of this invention to provide a sample holder with the handling support adapted, optionally, to receive and support a septum through which a liquid, volatile, or gaseous sample material may be loaded into a closed sample holder by insertion of a hypodermic needle.

The present invention fulfills the above objects and overcomes limitations and disadvantages of prior art solutions to problems by providing a novel sample holder for liquid or powder material for X-ray spectroscopic analysis that allows a technician to easily lift and maneuver a sample holder in preparation for the X-ray analysis. The sample holder comprises a body having an outer wall, and a transverse wall having an outside surface secured to the outer wall, the outer wall and the transverse wall defining a cell adapted to contain the sample material. The outer wall includes a rim portion that defines an open face of the body and of the cell. A handling support for the sample holder includes a stem member that extends substantially perpendicularly outwardly from the center portion of the outside surface of the transverse wall and a top member affixed to the end of the stem member. The handling support is for providing a grip for a tool used in the process of raising or lowering the sample holder. The handling support is equally accessible to the tool completely around the handling support. A film maintains a taut surface for the sample material for X-ray analysis and seals the open face of the cell. The film is secured to the outer wall of the body of the sample holder. The outside surface of the transverse wall is preferably substantially cylindrical and is axially aligned with the circular outside surface. The top member is preferably a cylindrical disk member affixed to and axially aligned with the stem member. The disk member has a diameter greater than the diameter of the stem member and less than the diameter of the circular outside surface. The transverse wall can have a vent for passing gas between the cell and the outside of the body when the sample holder is in a vacuum environment. The vent is preferably baffled so as to inhibit the passage of sample material from the cell. The sample holder can have a well defined by the transverse wall and another rim portion opposite to the rim portion mentioned. The well is adapted to contain sample material that exudes from the cell through the baffled vent. The face of the cell is sealed by single layer of film.

The sample holder can contain an absorbent material that contains a liquid sample disposed at the center of the open face. Inner and outer film layers sandwich the liquid sample material.

The sample holder can include a cap member that includes the transverse wall. Mounting means associated with the periphery of the transverse wall and the outer wall is adapted to removably secure the cap member to the body with sufficient strength to hold the body to the cap when the sample holder is being lifted with the tool at the handling support. When a sample holder with a cap member has a vent or a baffled vent, the transverse wall of the cap is disposed across the body of the holder so as to define a well along with the outer wall of the body of the holder. The stem and the disk are positioned within the well.

The sample holder and preferably its handling support is adapted to optionally receive and support a septum through which a liquid, volatile, or gaseous sample material may be loaded hands-on or by remote robot mechanism by insertion of a hypodermic needle into a fully closed sample holder.

The invention will be more clearly understood from the following description of specific embodiments of the invention together with the accompanying drawings, wherein similar reference characters denote similar elements throughout the several views, and in which FIG. 1 is a top view of a sample holder with a vented cap with a handling support;

FIG. 16 is a top view of handling support tweezers with a locking cylinder in a locked closed position;

FIG. 17 is a top view of handling support tweezers in a locked open position;

FIG. 18 is a partially sectional view of a sample holder being lowered into a cell positioner of a spectroscopic array with tweezers in a locked closed position gripping the handling support;

FIG. 19 is a partially sectional side view of a sample holder in position in a cell positioner with tweezers still gripping the handling support.

Figure 1:
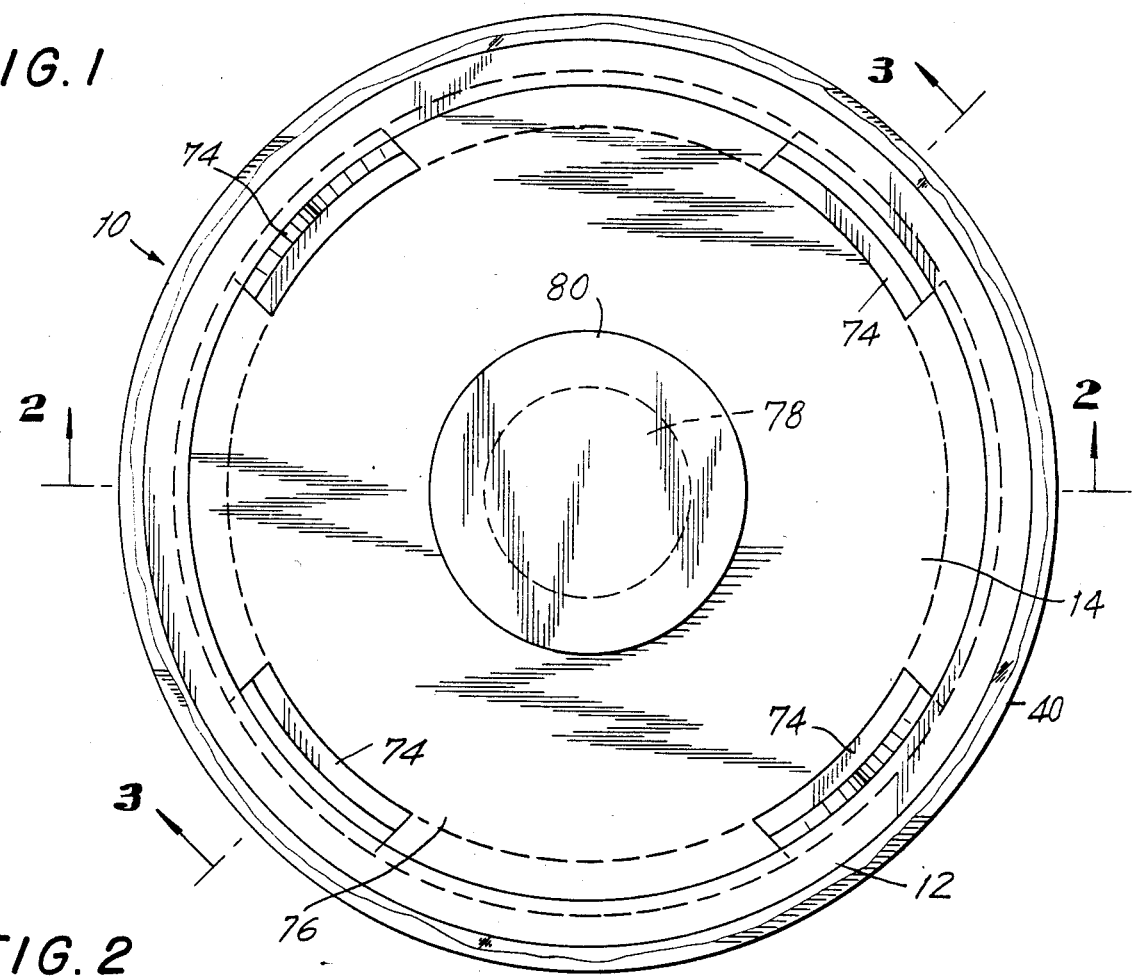

Reference is now made in detail to the drawings wherein reference numerals are correlated to various elements of the invention as described below.

Figure 2:
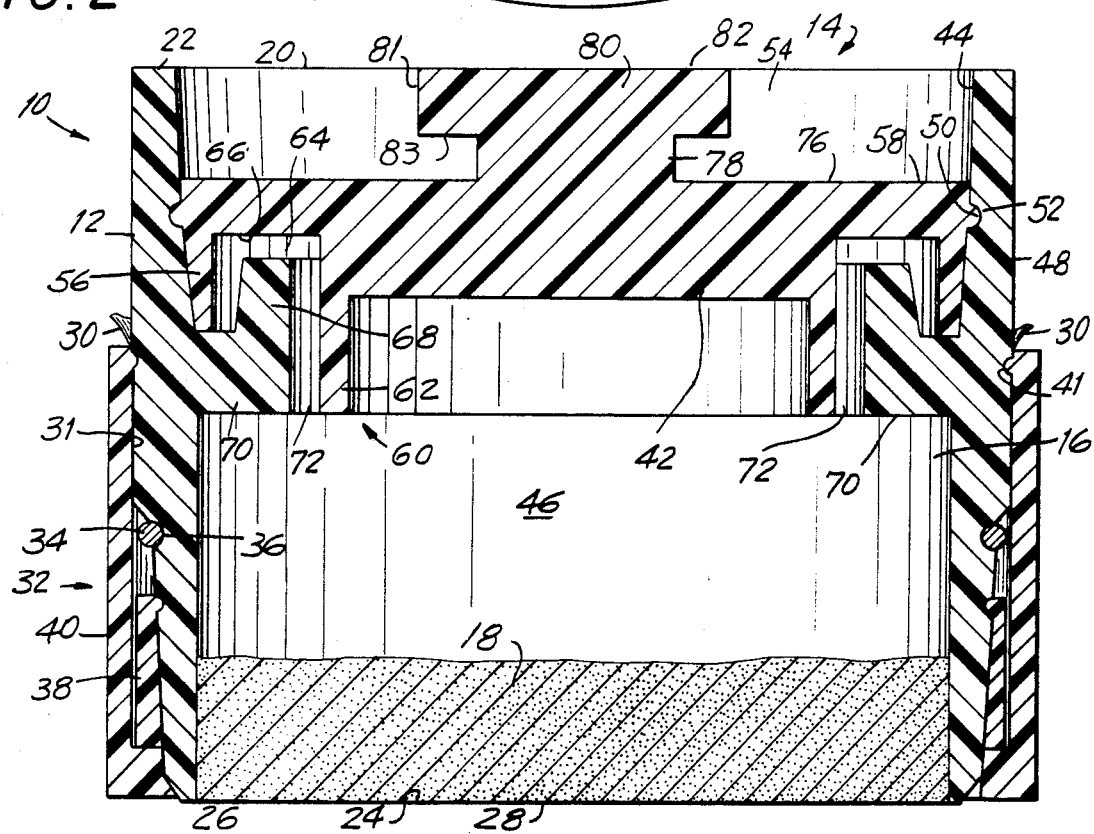
FIG. 2 is a sectional view taken through line 2—2 of FIG. 1.
Figure 3:
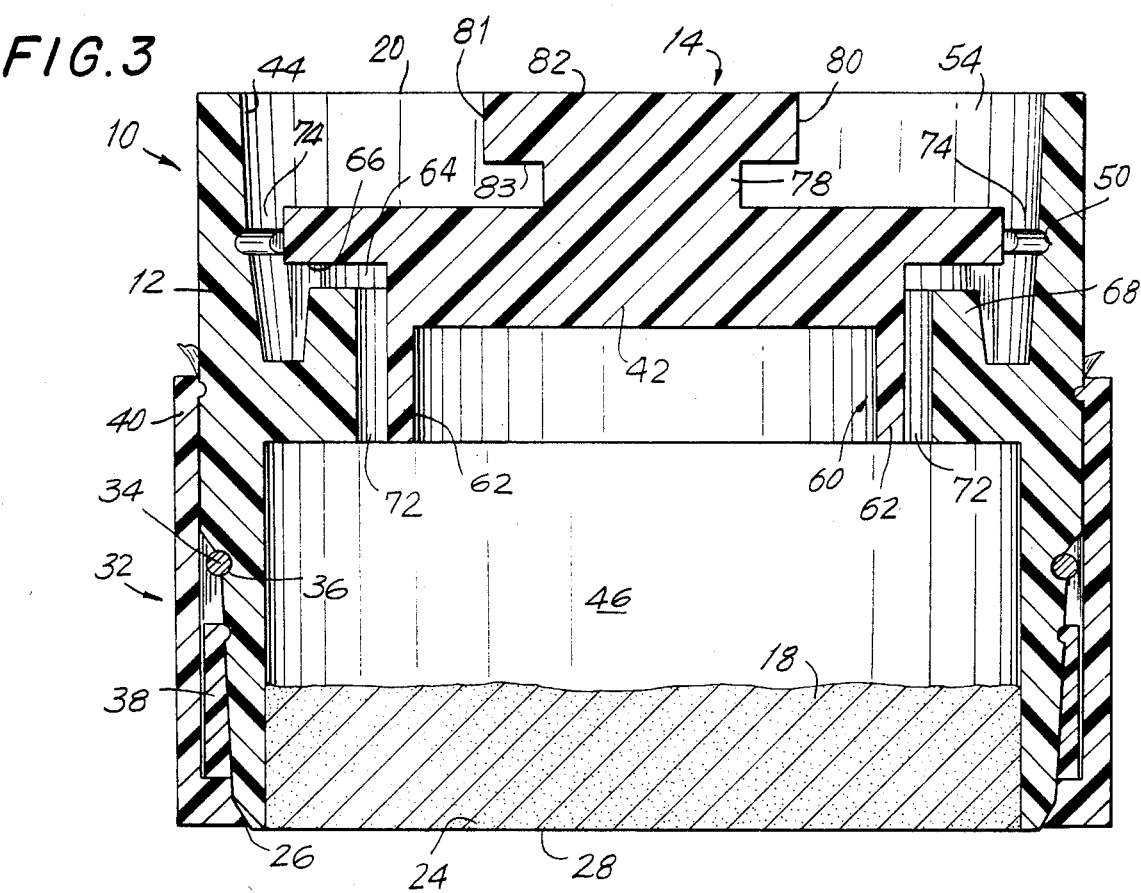
FIG. 3 is a sectional view taken through line 3—3 of FIG. 1.

FIG. 1 is a top view of a sample holder 10 including a generally cylindrical body 12 and a cap 14 snap-fitted onto body 12 as seen in FIGS. 2 and 3. Body 12 forms a generally cylindrical chamber 16 adapted to receive and hold a sample material 18, which can be a liquid, a viscous material, or a powdered material. For purposes of illustration, sample 18 is shown as a powdered substance. Body 12 forms an upper circular face 20 across the top rim 22 of cell 16 and an opposed lower circular face 24 across the lower rim 26 of chamber 16. Upper and lower faces 20 and 24 each lie in approximately parallel planes. A plastic film 28 is stretched tightly across lower face 24. The skirt 30 of film 28 is pressed, or clamped, around the outer surface 31 of body 12 by a film securing system 32 so that film 28 is stretched tightly across lower face 24 and chamber 16 is sealed across lower face 24.

The preferable film securing system 32 shown in the embodiments comprises an O-ring 34 positioned in a circumferential recess 36 located in the lower outer surface portion of body 12, an inner cylindrical film ring 38 positioned between and spaced from O-ring 24 and lower rim 26, and an outer cylindrical ring, or closure sleeve, 40 that presses against surface 31 above ring 38. Film 28 is stretched against lower face 24 by means of its skirt 30 being drawn against surface 31 of body 12 by O-ring 34 and inner film ring 38. The loose end of skirt 30 extends past the top rim of closure sleeve 40. Closure sleeve 40 presses the end portion of film skirt 28 to surface 31 at circumferential snap-in connection 41 of sleeve 40. Closure sleeve 40 has a bottom flange 43 that serves to press inner film ring 38 tightly against the surface 31. As seen in FIG. 2, the outer surface of body 12 tapers outwardly from lower rim 26 so as to snugly receive inner film ring 38 during mounting.

Cap 14 includes a generally circular top wall portion 42 that extends across chamber 16 and forms a tight sealing fit against the circular inner surface 44 of chamber 16. Top wall 42 is spaced below upper face 20 and generally forms with inner surface 44 a lower portion, or cell, 46, in which is contained sample material 18. The outer circumferential surface 48 of top wall 42 forms a circumferential snap-in fitting, or bead, 50 that is adapted to snap-fit into hemispherical circumferential slot 52 formed in inner surface 44. The snap-in fitting is of sufficient strength to secure body 12 to cap 14 when cap 14 is being lifted so that body 12 and cap 14 remain together as a unit. Top wall 42 also forms with inner surface a well, or reservoir, 54. A circumferential outer flange 56 depends downwardly at an inward taper from the outer rim portion or periphery, 58 along tapered inner surface 44 of body 12 to provide a further firm fit between body 12 and cap 14.

A baffle system 60 is used to allow passage of air from cell 46 and to inhibit movement of liquid or powder sample material 18 from cell 46 when holder 10 is placed in a vacuum environment (not shown) used in certain spectroscopic analysis techniques. Baffle system 60 is cooperative with interrelated mounting systems, one associated with inner surface 44 of body 12, in particular inner surface 44, and the other associated with the periphery 58 of wall portion 42. The two mounting systems cooperate to position cap 14 with body 12 when they are engaged. The interrelated structure of baffle system 60 and the two mounting systems will become clear in the discussion that follows. Baffle system 60 as shown in the embodiment shown in FIGS. 2 and 3 includes a circumferential inner flange 62 that depends downwardly from an inner portion of top wall 42. Inner flange 62 is spaced from outer flange 56 and extends to a horizontal plane vertically below that of outer flange 56. A circular groove 64 is formed between inner and outer flanges 62 and 56 and the peripheral undersurface 66 of top wall 42. Baffle system 60 further includes an upwardly extending circular flange 68 that is connected to a circular connecting portion 20 that in turn is integral with the outer wall of body 12. As shown in FIG. 2, upward flange 68 is positioned in groove 64 and spaced from both inner and outer flanges 62 and 56 so as to form an inverted U-shaped passageway 72. Movement of air, fluid, or powder directly through passageway 72 is inhibited by outer flange 56 as shown in FIG. 2, while movement of air is allowed through passageway 72 through four opposed recesses 74 disposed at approximately right angles one to another as shown in FIGS. 1 and 3. Cap 14 as shown in FIGS. 1, 2, and 3 is a vented cap as distinguished from a closed cap to be discussed in detail below with reference to the embodiment of FIG. 6.

A cylindrical stem 78 extends outwardly from circular flat top surface 76 of top wall 42, which is approximately in a plane parallel to upper and lower open faces 20 and 24. Stem 78 is axially aligned with circular top surface 76 of top wall portion. As shown in FIGS. 2 and 3, stem 78 extends perpendicularly upwards, the usual orientation of holder 10 during X-ray analysis. A disk top member 80 is affixed to and axially aligned with the top of stem 78 and has a circular flat top surface 82 approximately parallel with top surface 76 of top wall portion 42 of cap 14. Disk member 80 is cylindrical and includes a circumferential cylindrical side wall 81 and a toroidal flat bottom wall 83 that intersects stem 78 and is substantially parallel with top surface 82. Side wall 81 has sufficient thickness so that disk member 80 will brace holder 10 when stem member 78 is grasped by a tool in the process of raising or lowering holder 10. Also, disk member 80 is to have sufficient strength to lift holder 10 when disk member 80 is directly grasped by a tool. For example, the height of side wall 81 in FIGS. 2 and 3 is approximately 0.75 in. Disk member 80 has a diameter greater than the diameter of stem 78 and less than the diameter of circular top surface 76 of top wall portion 42. Disk member 80 preferably has a flat circular top surface 82 that preferably lies in the same plane as upper face 20, as shown in FIGS. 2 and 3, or is aligned below upper face 20. Stem 78 is preferably relatively thick as compared to disk member 80; that is, the diameter of stem 78 is not much less than the diameter of disk member 80. The size of a holder body varies in accordance with usage. The diameter of the holder body shown in FIGS. 2 and 3, for example, often varies between 1 and 2 in. The height of the holder cell can in turn vary between 0.75 in. and 1.75 in. The diameter of stem 78 will generally be fixed to approximately 0.25 in. The height of stem 78 is preferably kept to an operative minimum in order to keep well 54 at a minimal height, but could vary from 0.15 in. to 0.22 in.

Disk member 80 is basically for gripping with a tool as will be discussed later and is thus basically a gripping member. It is to be noted that the central position of disk 80 and its circular configuration set over circular stem 78 allows a tool to grip disk 80 over an access area of any angle. Stem 78 also allows a tool to grip the stem from any angle with disk 80 acting as a hold down member.

Figure 4:
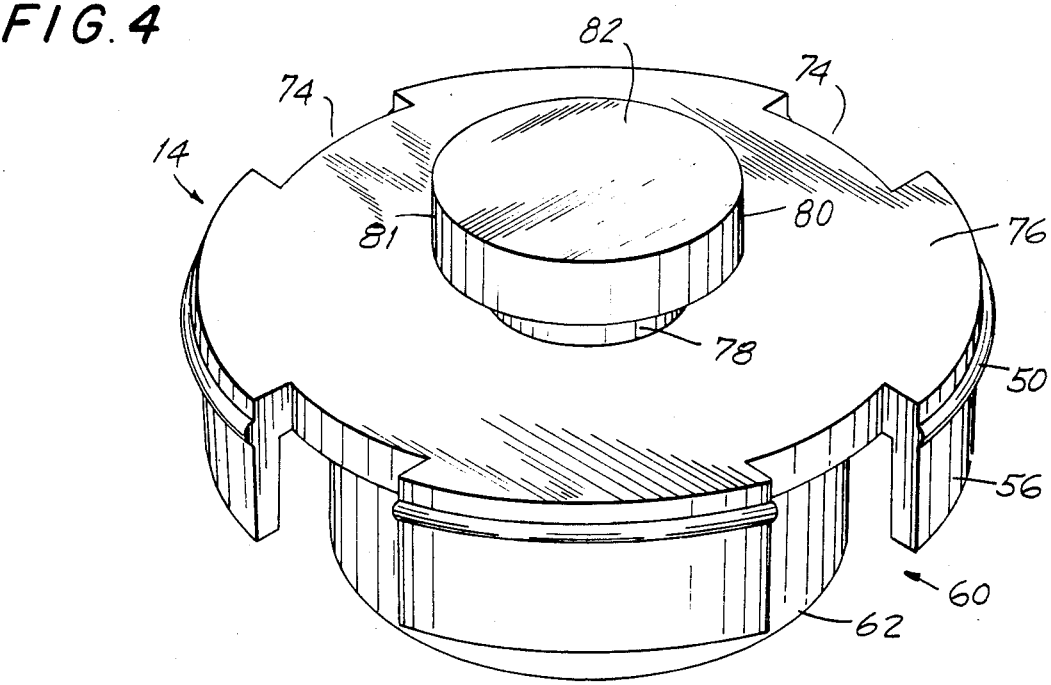
FIG. 4 is a perspective view of a vented type cap with a handling support.
Figure 5:
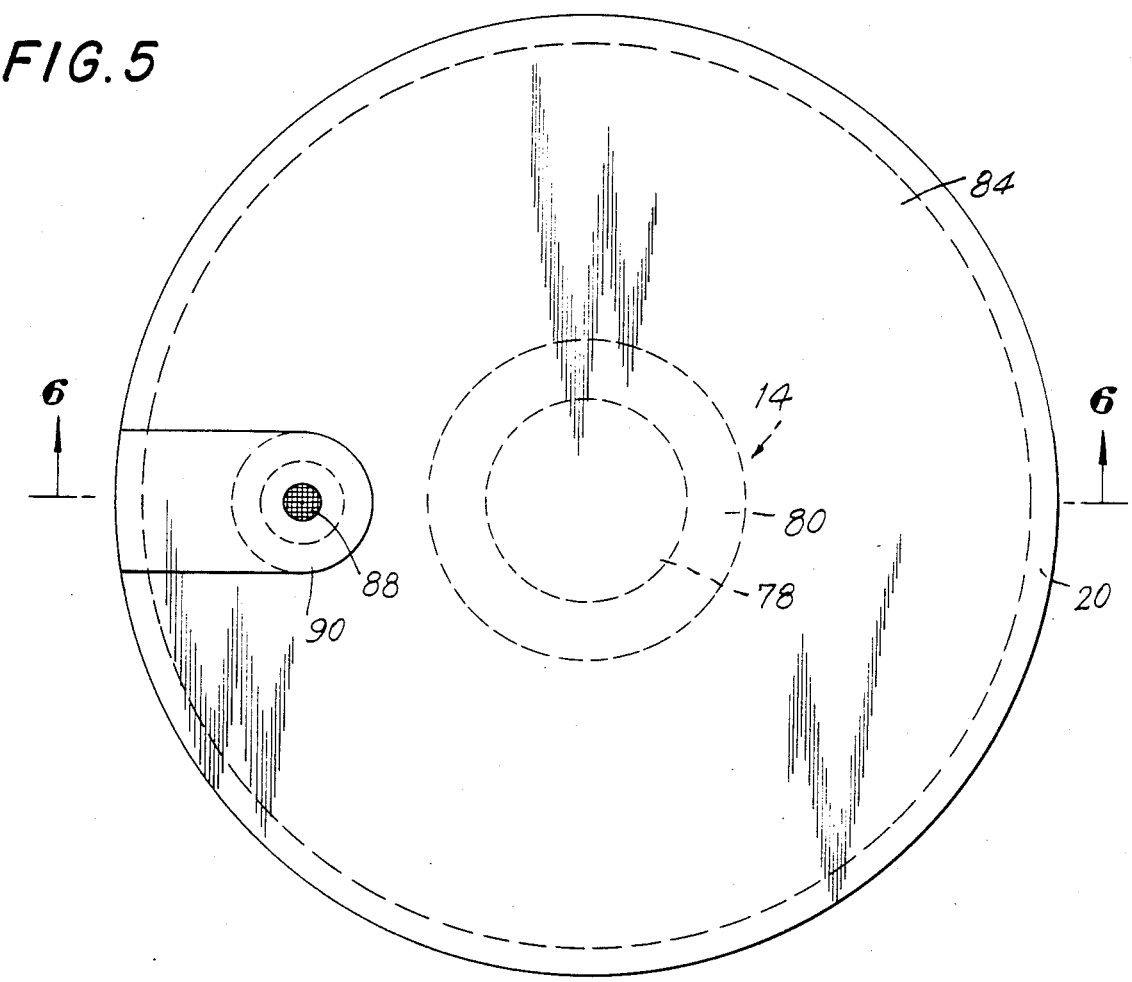
FIG. 5 is a fragmented sectional view of a sample holder with a vented cap with a handling support and a top cover.
Figure 6:
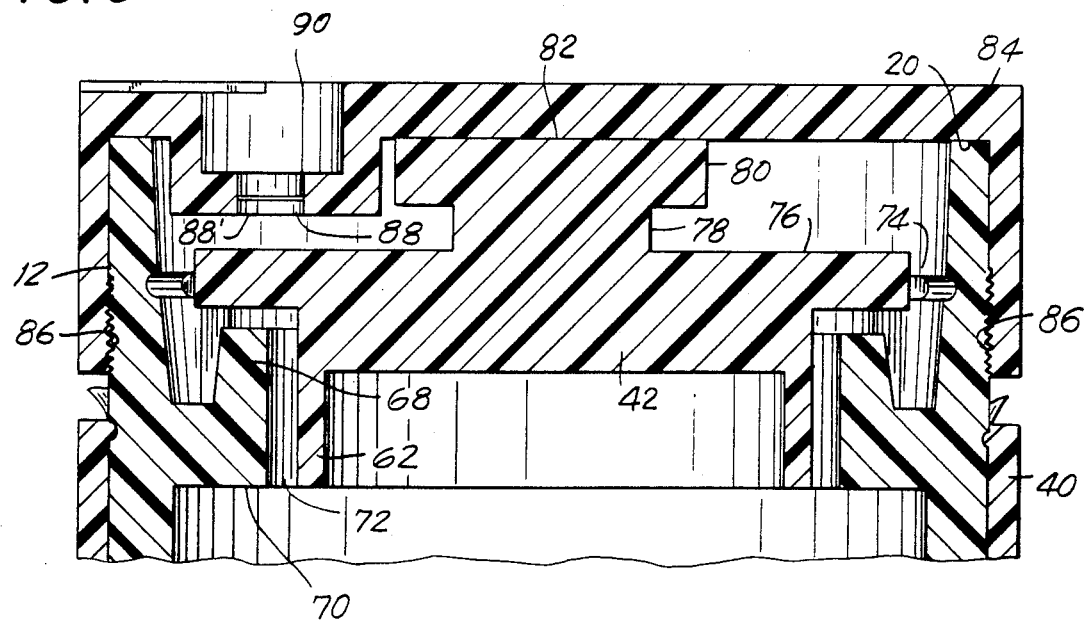
FIG. 6 is a top view of a sample holder with a sealed cap with a handling support and cover.

The alignment of top surface 82 with or below upper face 20 makes possible the placement of a top cover 84 over the top of body 12 and cap 14 in the embodiment shown in FIGS. 5 and 6, which has a cap analogous to the cap shown in FIG. 4. Top cover 84 is screwed onto body 12 by way of threads 86. A circular stainless steel non-wetting filter 88 on one side of top cover 84 is positioned at the bottom of a circular recess 90 that is formed in the top of top cover 84. Stainless steel non-wetting filter 88 allows passage of air or other gas but not of liquid if holder 10 is positioned in a vacuum chamber. The applicant notes here that in a certain spectroscope machines the cell positioner orients film face 28 upwards, that is, the inverse of the alignment of body 12 in FIGS. 2, 3, and 4, and the X-ray is directed at the top of holder 10. In such a case, cover 84 is disposed at the bottom of holder 10, and either the non-wetting stainless steel filter or alternatively a punchout member 88 in lieu of filter 88 may be kept intact so that inverted cover 84 acts as a reservoir if a liquid sample is in cell 46. In such an event cap 14 would not be a vented cap as shown in FIGS. 1, 2, 3, and 4, but a closed cap as shown in FIG. 6, which is described below.

It is to be particularly noted that when sample holder 10 is being loaded or unloaded, or positioned by a remote or a robot tool, cap 14 must either be pressed down upon body 12 so that the snap-in connection can be made of bead 50 being snapped into slot 52, or be pulled up from body 12 so that the snap-in connection can be disconnected by way of pulling bead 50 from slot 52. For the mounting operation, lower rim 26 would basically be the support for body 12, since lower rim 26 would be set upon a resistant foundation. It is to be noted that the lower rim of closure sleeve 40 must not extend below lower rim 26 of body 12 so as to leave lower rim available as a mounting support. Similarly, top rim 22 of body 12 acts as a top hold-down support when cap 14 is being removed from body 12. Top rim 22 would be positioned under a suitable mechanism against which the rim would press as the cap was being pulled loose from the body prior to an unloading operation.

Figure 7:
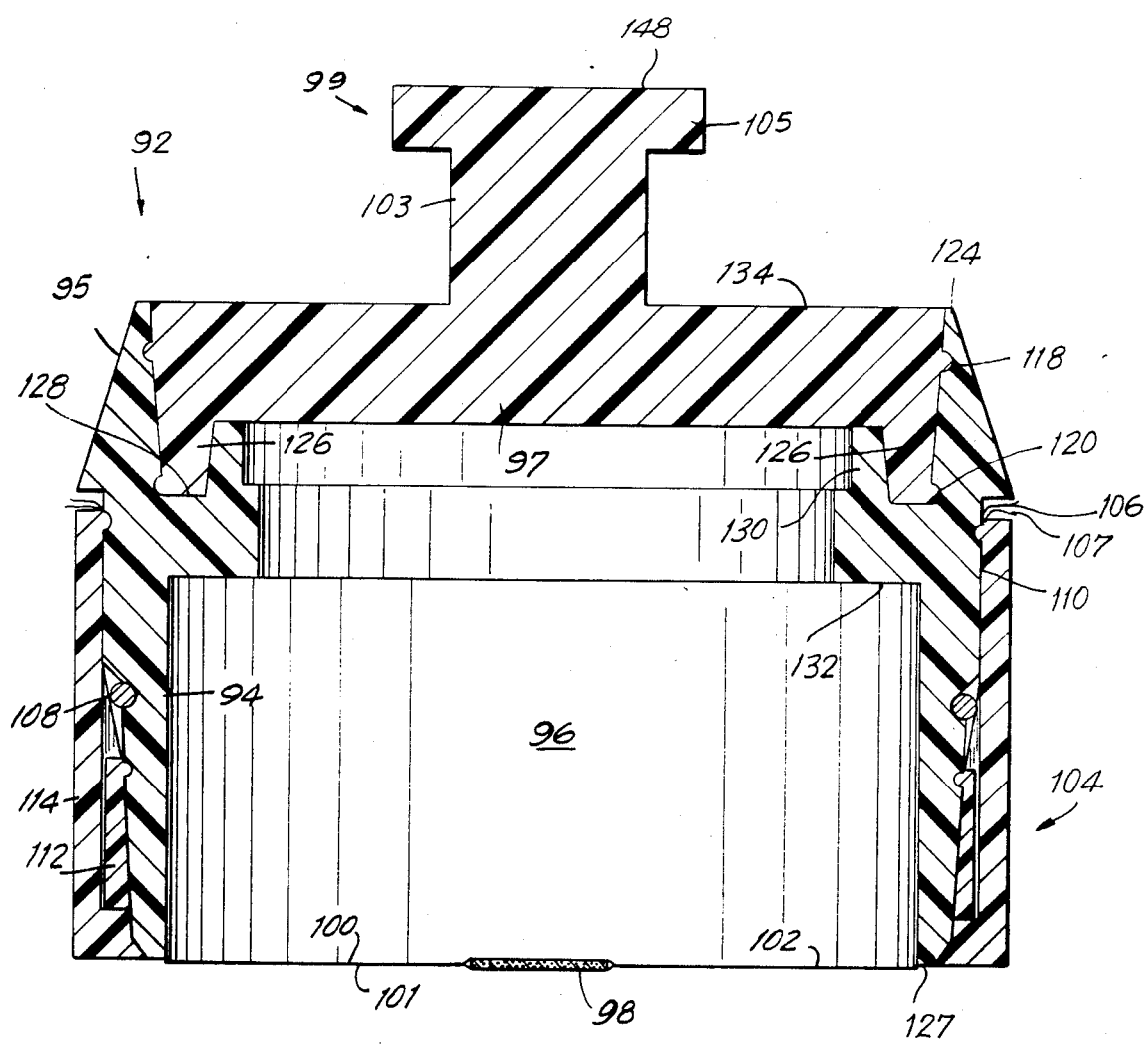
FIG. 7 is a sectional view of a sample holder with unvented cap and handling support.

FIG. 7 illustrates a sample holder that is used in special applications for spectroscopic analysis relating to remote access X-ray and radioactive material. Holder 92 comprises a generally cylindrical body 94 forming a generally cylindrical cell formed in part by a horizontal transverse circular wall 97 of a sealed cap 99 that includes a handling support comprising a cylindrical stem 103 extending from the center of top surface of transverse circular top wall 97 topped by a cylindrical disk 105. A circumferential inwardly tapered support piece 95 integral with body 94 is disposed around the top of body 94 and is adapted to be press fitted into a special positioning cell of an array of a spectroscope for remote X-ray analysis. A sample material is impregnated in a piece of filter paper 98 that is sandwiched between inner and outer film layers 100 and 101. Filter paper 98 is positioned at the center of lower face 102 of body 94. Film layers 100 and 101 in turn are stretched across lower face 102. A film securing system 104 presses film skirts 106 and 107 of film layers 100 and 101 respectively against the outer surface of body 94. Film securing system 104 is directly analogous to film securing system 32 described previously with regard to the embodiment shown in FIGS. 2 and 3, namely, an O-ring 108 positioned in a circular recess formed in the outer surface 110 of body 94, an inner film ring 112, and an outer ring, or sleeve, 114, with skirts 106 being pressed against outer surface 110 by O-ring 108 and skirts 106 and 107 by inner film ring 112, the latter two elements of which are pressed against outer surface 110 by closure sleeve 114, which in turn presses film skirts 100 and 101 to body 94. Sealed cap 99 is snap-mounted onto the top portion of holder 92 by way of a pair of cooperating spaced circular snap-on upper and lower connections 118 and 120 at the periphery of top wall 122 of cap 116 and the inner surface 124 of the top portion of cell 96. Top wall 97 is disposed across the upper face of body 94 and its periphery is in press contact with inner wall surface 124. A flange 126 extends downwardly from the periphery of top wall 122 into a tight fit into a circular upwardly facing recess 128 formed by an upwardly extending flange 130 affixed to an inwardly disposed ledge 132 in turn connected to the upper portion of body 94. Downward flange 126 is pressed against the surfaces of recess 128 so as to additionally seal cell 96 and prevent passage of any of sample 98 from the cell. Downward flange is preferably tapered inwardly and recess 128 is preferably tapered outwardly so as to firmly wedge downward flange 126 into recess 128.

Top wall 97 of cap 99 has a circular flat top surface 134, which is preferably approximately in a plane parallel to lower face 102. Cylindrical stem 103 is axially aligned with circular top surface 134 and extends perpendicularly from surface 134. As shown in FIG. 7, stem 103 extends upwardly, in accordance with the usual orientatin of holder 92. Cylindrical disk top member 105 is affixed to and axially aligned with the top of stem 103 and is parallel with top surface 134. Disk member 105 has sufficient thickness to support holder 92 when disk member 105 is used to lift holder 92. For example, the diameter of disk member 105 shown in FIG. 6 is approximately 0.9 in. Disk member 105 has a diameter slightly greater than the diameter of stem 103 and less than the circular top surface 134. Disk member 105 preferably has a flat circular top surface 148 that preferably lies approximately parallel to circular top surface 134. Stem 103 is preferably relatively thick as compared to disk member 105; that is, the diameter of stem 103 is not much less than the diameter of disk member 105. The embodiment shown in FIG. 7 indicates, for example, a diameter of stem 103 in the order of magnitude of 0.25 in. and a diameter of disk member 105 of 0.375 in. The height of stem 103 in FIG. 4 can be greater than of stem 78 in FIGS. 2 and 3 for the reason that holder 92 does not include a well. The height of stem 103, for example, is shown to be approximately 0.18 in., that is, about three times the height of stem 78.

It is worth mentioning here that downward outer flange 126 of sealed cap 99 could replace downward outer flange 56 of vented cap 14 of holder 10 and so seal off the inner recess of U-shaped passageway formed by upward flange 78, connecting portion 70, and inner surface 44 of chamber 16 of holder 10. Alternatively, cap 14 of holder 10 could eliminate recesses 74 shown in FIGS. 1 and 3. Preferably, a sealed cap for baffle system 60 of holder 10 can be formed by including a combination of the above, namely eliminating recesses 74 and enlarging downward flange 56 to the configuration of downward flange 126 of FIG. 7.

The remarks made earlier regarding mounting of cap 14 from body 12 likewise apply in general to body 94 and cap 99. That is, when cap 99 is being snapped onto body 94 at snap-in connections 118 and 120, the lower rim 127 of body 12 that defines lower face 102 acts as a support, or hold down, during the mounting operation, as rim 127 is pressed against a foundation.

Figure 8:
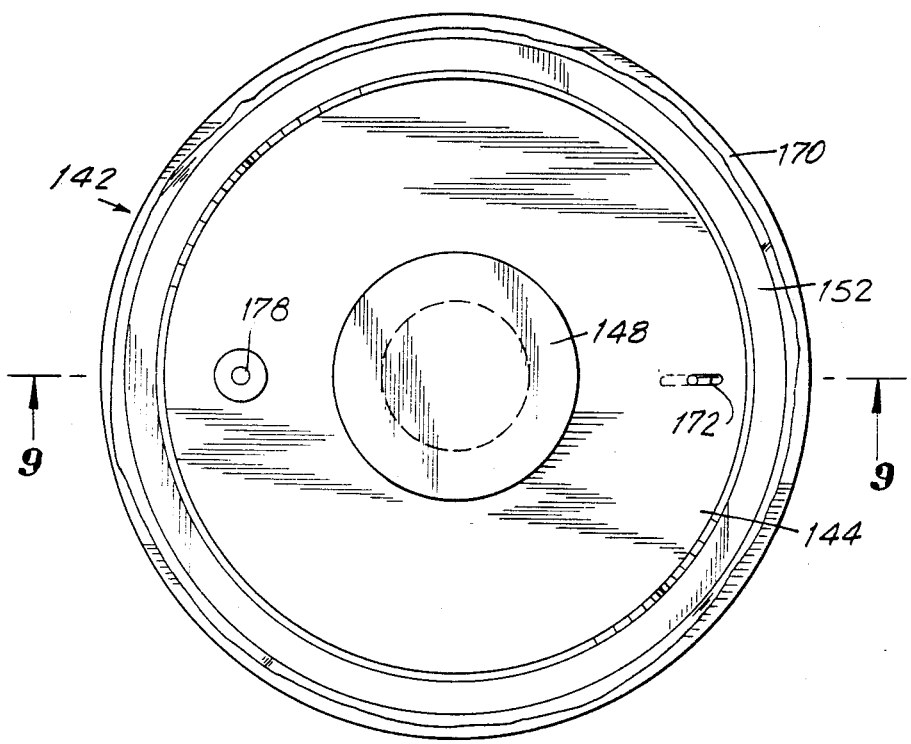
FIG. 8 is a top view of a sample holder with an integral vented top wall with a handling support.
Figure 9:
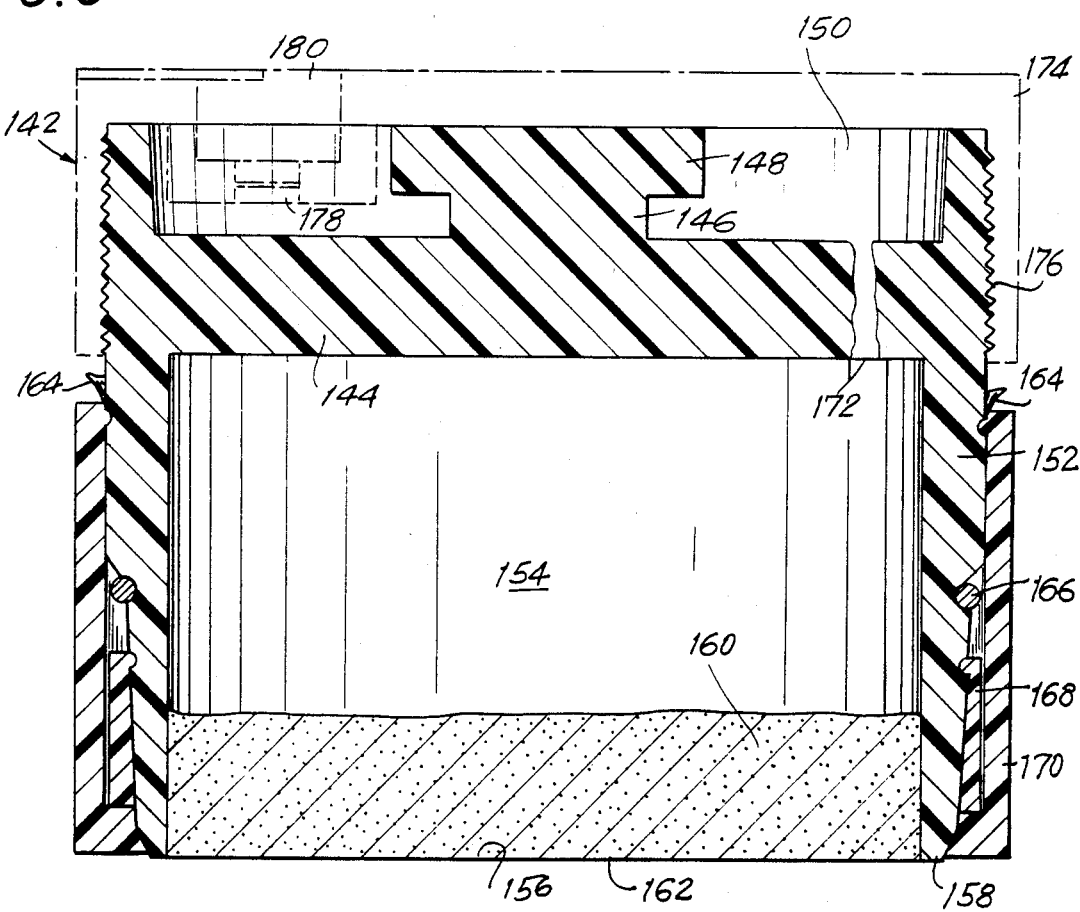
FIG. 9 is a sectional view taken through line 9—9 of FIG. 8.

FIGS. 8 and 9 illustrate a sample holder 142 having an integral transverse wall 143 with a centered cylindrical stem 146 topped by a centered cylindrical disk top member 148 that acts as a gripping member. Sample holder 142 is analogous to sample holder 10 shown in FIGS. 1, 2, and 3, except that sample holder 142 has no separate, or distinct, cap 14 as does sample holder 10.

Sample holder 142 forms a reservoir 150 defined by outer cylindrical wall 152 of holder 142 and transverse wall 144. Also, sample holder 142 forms a generally cylindrical cell 154 defined by transverse wall 144 and outer wall 152. Cell 154 forms a bottom face 156 defined by circular bottom rim 158 of outer wall 152. Cell 154 contains a powdered sample 160 that lies atop a taut film surface 162 which has a film skirt 164 secured to the outer surface of outer wall 152 by a film securing system comprising an O-ring 166, an inner film ring 168, and a closure sleeve 170 that fits over O-ring 166 and ring 168 but does not come into contact with them in the same manner as securing system 32 shown in FIGS. 2 and 3. A spiral baffled vent 172 is shown extending on one side of transverse wall 144 from cell 154 to reservoir 150. A top cover 154 is shown in phantom lines in FIG. 9 secured to outer wall 152 by threads 176. Top cover 174 is directly analogous to top cover 174 shown in FIG. 5. Top cover 174 has a stainless steel non-wetting filter 178 at the bottom of a reservoir 180 formed in the top of cover 174. The handling support comprising stem 146 and disk member 148 can be gripped by a tool handled by a technician or by a remotely controlled robot arm. Complete 360 degree access to a tool is given by disk member 148 and stem 146.

Figure 10:
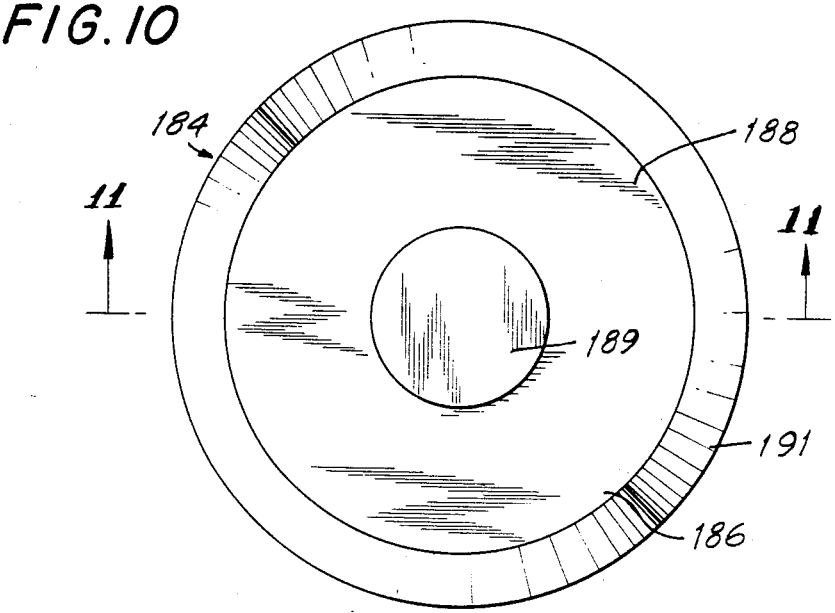
FIG. 10 is a top view of sample holder with an integral sealed top wall with a handling support.
Figure 11:
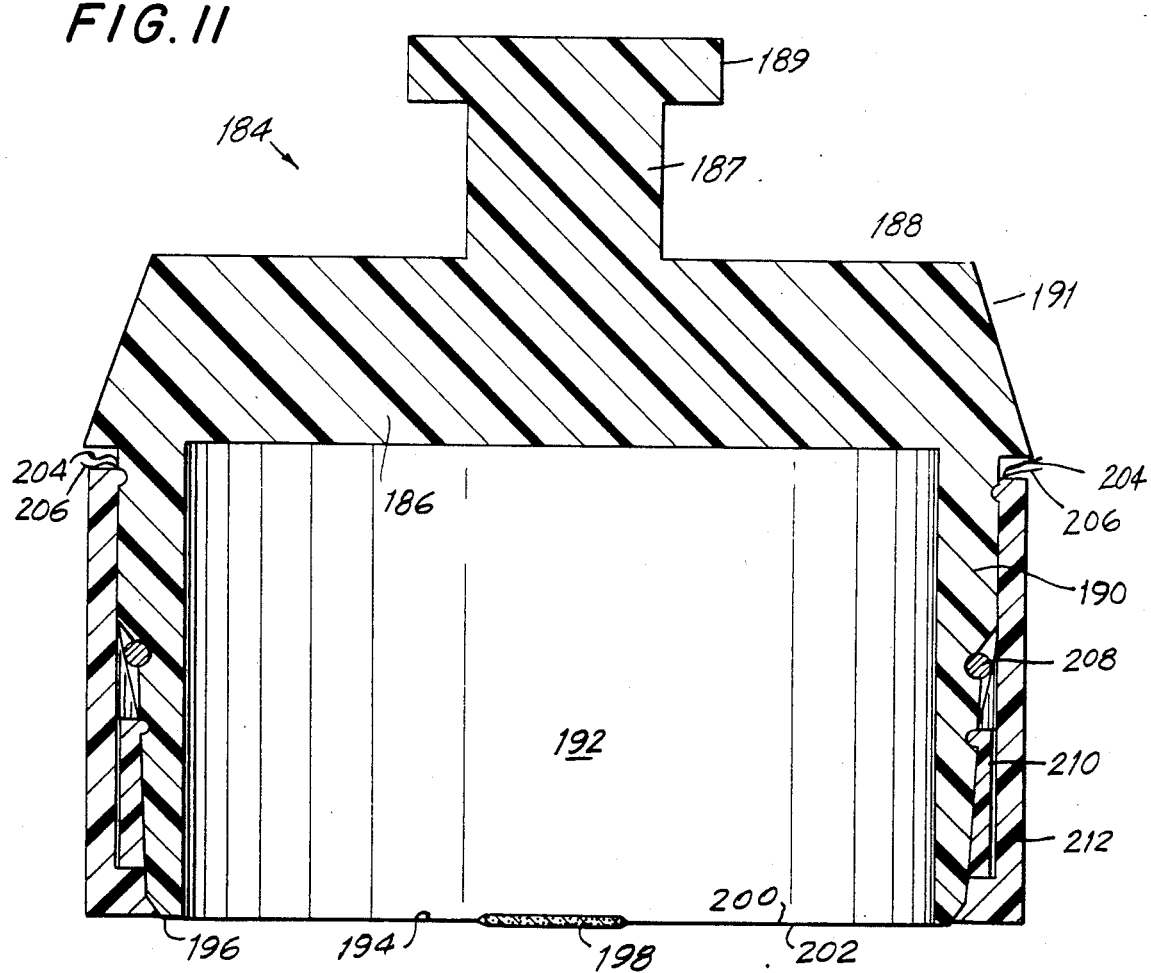
FIG. 11 is a sectional view taken through line 11—11 of FIG. 10.

FIGS. 10 and 11 illustrate a sample holder 184 that is generally analogous to sealed sample holder 96 shown in FIGS. 6 and 7. Sample holder 184 has an integrated top transverse wall 143 with a centered cylindrical stem 187 topped by a centered cylindrical disk top member 189 that acts as a gripping member. Top transverse wall 143 is connected to the top rim 188 of the cylindrical outer wall 190 of holder 184. Outer wall 190 forms a circumferential tapered pressing surface 191. Holder 184 forms a generally cylindrical cell 192 which is defined by outer wall 190 and top wall 186. Cell 192 has a bottom rim 196 of outer wall 190.

A piece of filter paper 198 impregnated with a liquid sample is positioned at the center of bottom face 194. An inner and an outer film surface 200 and 202 respectively are stretched taut across bottom face 194 and sandwich sample 198 between them. Inner and outer film skirts 204 and 206 of inner and outer films 200 and 202 respectively are secured to the outer surface of outer wall 190 by a film securing system comprising an O-ring 208, an inner film ring 210, and an outer closure sleeve 212. The film securing system of holder 184 is directly analogous to film securing system 104 for sample holder 96. The handling support comprising stem 187 and disk member 189 can be gripped by a tool handled by a technician or by a remotely controlled robot arm. Complete 360 degree access to a tool is given by disk member 187 and stem 189.

Figure 12:
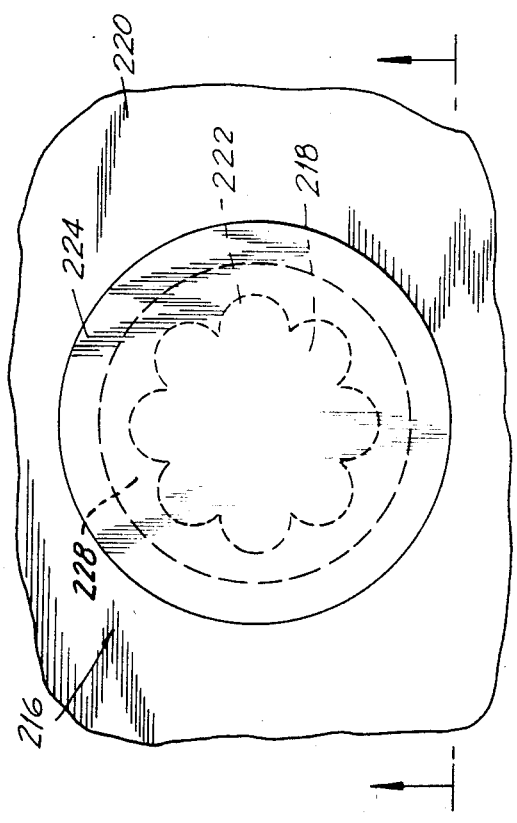
FIG. 12 is a fragmented top view of an alternate embodiment of a handling support.
Figure 13:
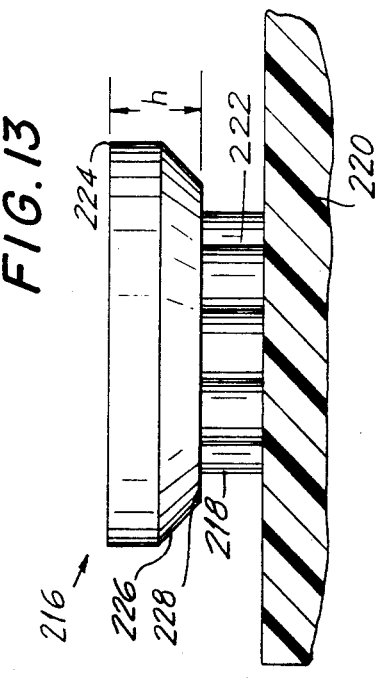
FIG. 13 is a sectional view taken through line 13—13 of FIG. 12.

FIGS. 12 and 13 illustrate slightly different embodiments of the disk and stem of the present invention. A cap 216 is shown that includes a stem 218 vertically positioned on the center of a top wall 220. Stem 218 is generally cylindrical but includes vertical flutings, or ribs, 222. A disk 224 is axially mounted over stem 218. Disk 224 is cylindrical having a diameter slightly greater than the outer diameter of stem 218. A chamber 226 is angled at about 45 degrees from about the mid point of the height h of the disk back to a short distance from the periphery of ribbed stem 218. Chamber 226 is convenient for molding purposes and chambered disk is within the scope of the present invention. Ribs 222 make grasping of cap 216 more secure when stem 218 is being gripped from the side. Disk 224 includes a ringed horizontal surface for a gripping tool.

Figure 14:
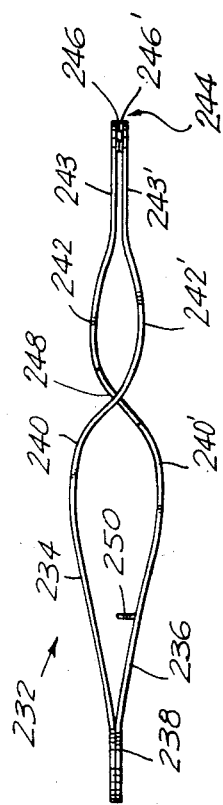
FIG. 14 is a top view of handling support tweezers.
Figure 15:
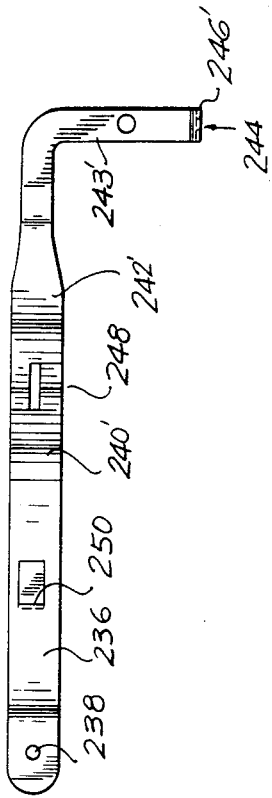
FIG. 15 is a side view of handling support tweezers.

FIGS. 14 and 15 illustrate a gripping tweezers 232. A pair of opposed, biased horizontal arms 234 ad 236 are joined at one end by a rivet 238. Each arm has first outward convolutions 240 and 240' respectively from rivet area 238, then convoluted back in a crossover to second outward convolutions 242 and 242' respectively, and then return to vertical fingers 243 and 243' respectively that terminate in pinching portions, or jaws 244 respectively, which have opposed inner grips 246 and 246'. First outward convolutions 240 and 240' are horizontally mated at their crossover 248 by way of having reduced heights of arms 234 and 236. A cross-stop 250 extends inwardly from first convolution 240' of arm 236 so as to limit the maximum opening of the inner of jaws 244. When second outward convolutions 242 and 242' are pressed together, jaws 244 are held together. Biased arms 234 and 236 are biased so as to hold jaws 244 together in the biased mode. When first outward convolutions 240 and 240' are pressed together, jaws 244 are forced open against the bias.

A locking cylinder 252 forming a cylindrical bore 254 is shown in FIGS. 16 and 17. Locking cylinder 252 is shown in a gripping mode in FIG. 16 wherein bore 254 locks arms 234 and 236 together at second convolutions 242, 242' so that grips 246, 246' of jaws 244 are pressed, or locked, together.

FIG. 17 shows locking cylinder 252 in a release mode wherein bore 254 locks arms 234 and 236 together at first convolutions 240, 240' so that grips 246, 246' of jaws 244 are forced, or locked, apart. Locking cylinder 252 can be slid between the gripping or release modes by a technician or by a remotely operated robot tool. It is of course possible to operate tweezers 232 by hand in the manner described with locking cylinder 252.

Application of tweezers 232 is illustrated in FIGS. 18 and 19 where grips 246 and 246' are placed around a disk 256 over a stem 258 of a 260 handling support with arms 234 and 236 being vertically aligned and grips 246 and 246' horizontally aligned around disk 256. FIG. 18 shows a sample holder 262 being lowered into a positioning well 264 of a holder positioning array 266 of a spectroscopic machine. Locking cylinder 252 is shown in its gripping mode around second convolutions 242, 242'. Locking cylinder 252 will then be slid back to its release mode so as to press jaws 244 apart to release their grip on disk 256.

Figure 20:
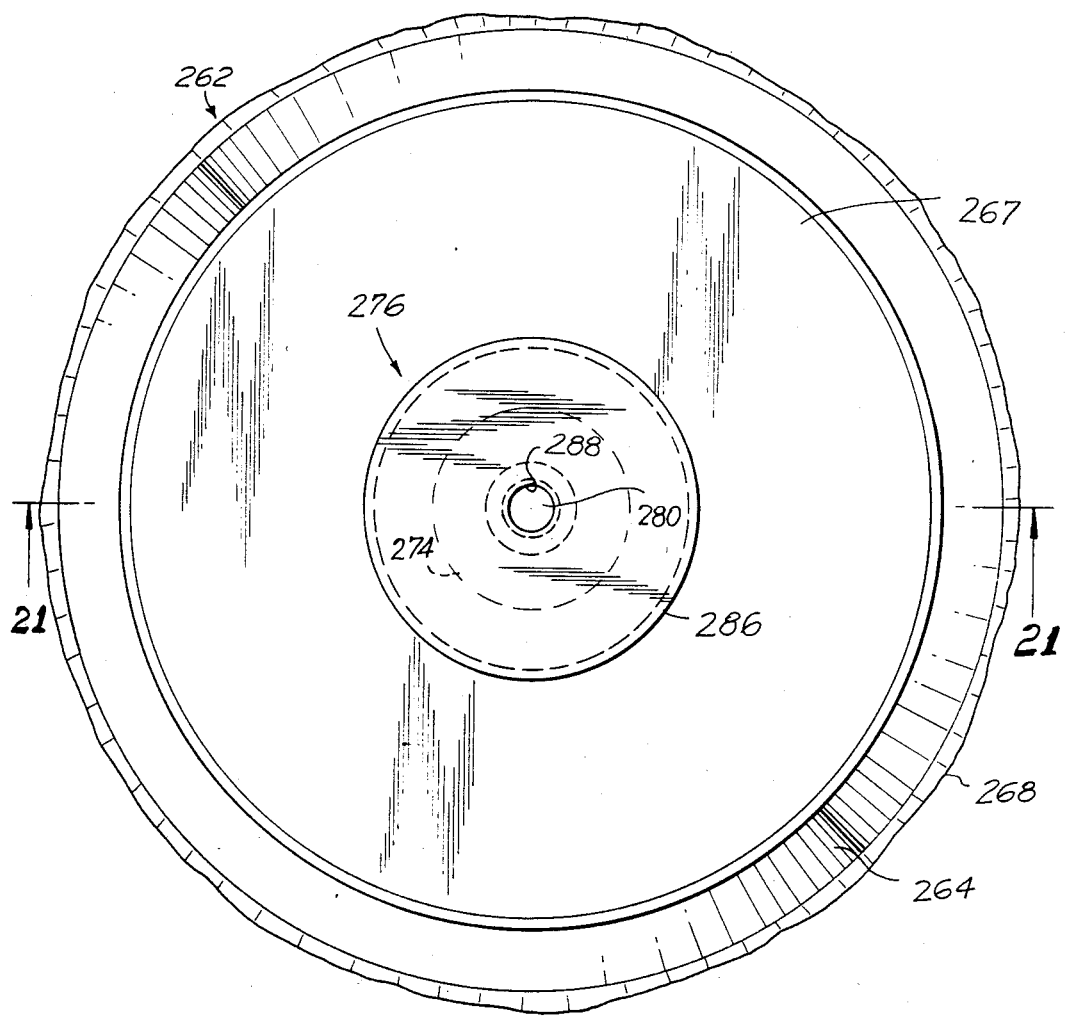
FIG. 20 is a top view of a sample holder with a handling support having a central passage sealed by a septum.
Figure 21:
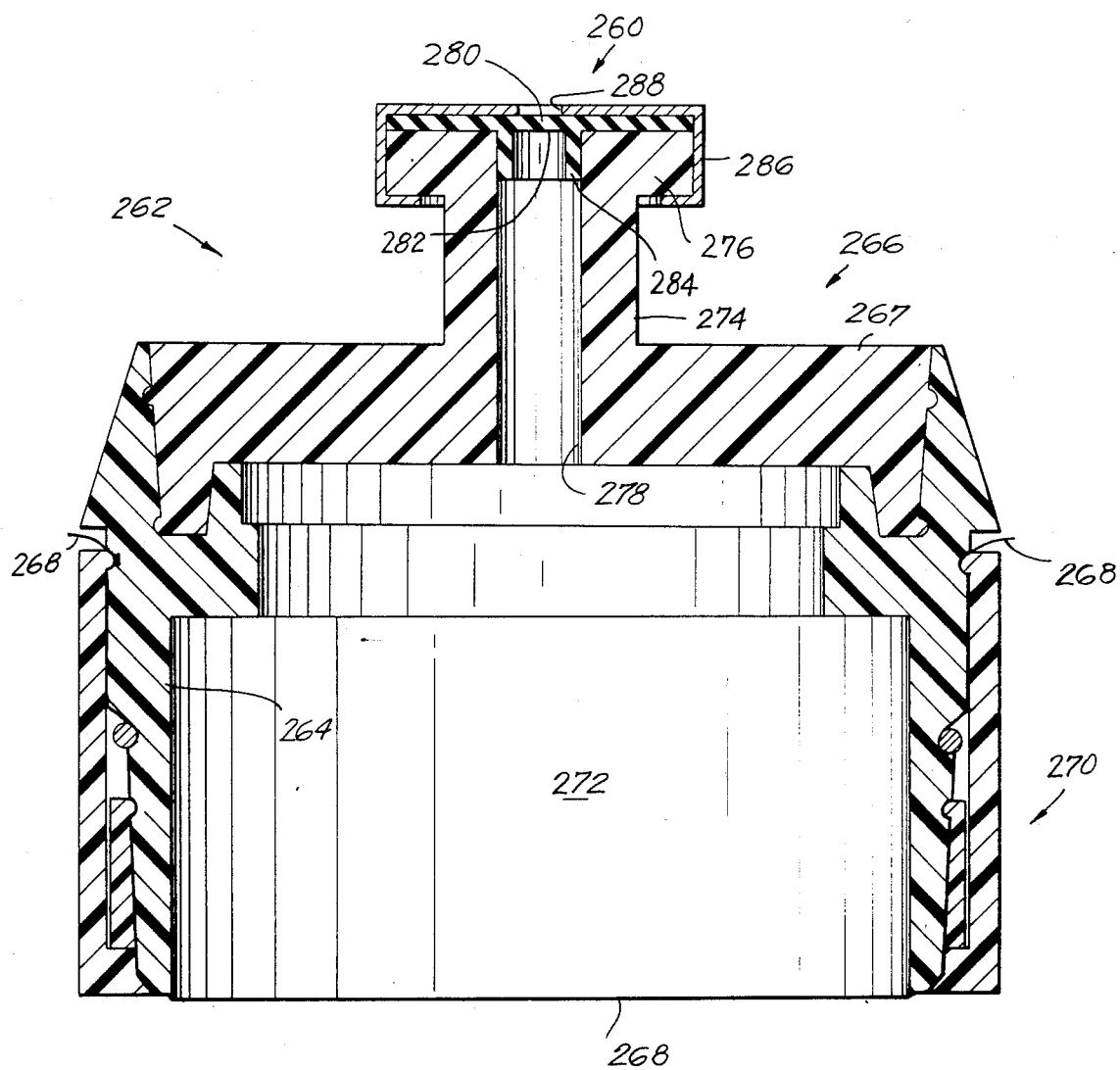
FIG. 21 is a view taken through line 21 of FIG. 20.
Figure 22:
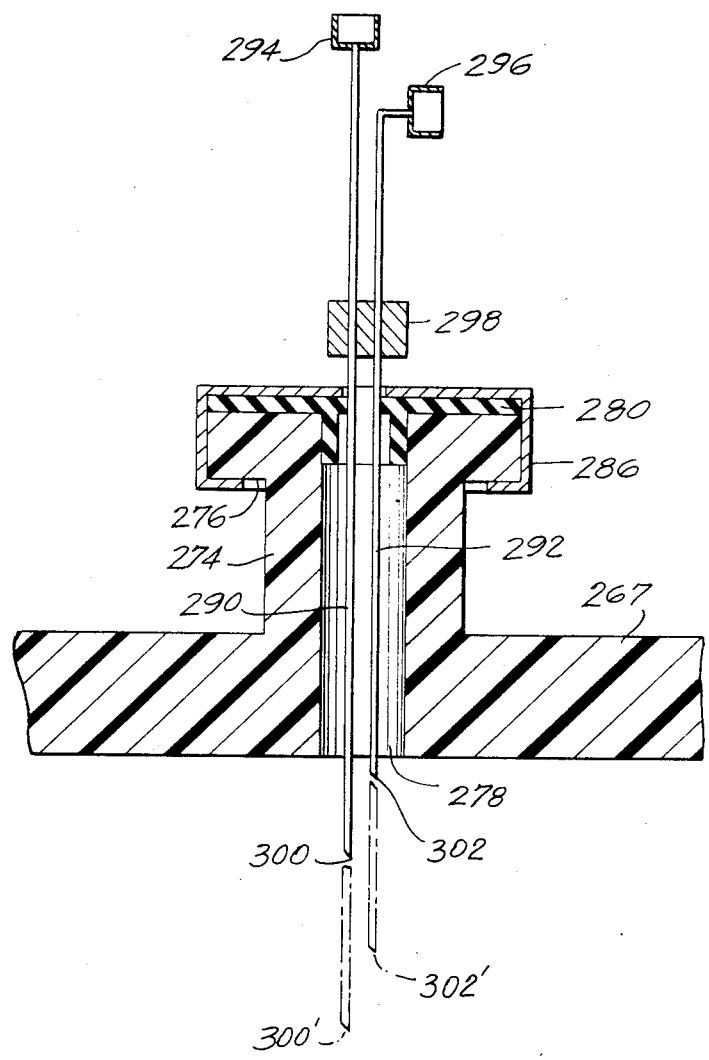
FIG. 22 is a detailed sectional view of the passage through the handling support with loading and unloading needles inserted through the septum.

FIGS. 20, 21, and 22 illustrate an especially interesting embodiment of the present invention that includes a loading system 260 that is adapted to allow liquid or gas samples to be injected into and held in the cell of a sample holder of X-ray analysis. A sample holder 262 generally analogous to the sample holders 92 and 184 shown in FIGS. 7 and 11 is shown in FIGS. 20 and 21. For purposes of illustration only, the embodiment of FIGS. 20, 21, and 22 follow the embodiment and discussion relating to FIG. 7 herein, although loading system 260 is applicable to all the fully sealable holders described previously including those of FIGS. 8 and 11. Holder 262 includes a generally cylindrical body 264 and a removable cap 266 that is removably snap-mounted to the top of body 264. Cap 266 includes generally cylindrical top wall 267 which has extending snap mountings about its periphery for attachment to body 264. A single film strip 268, which is secured to body 264 by film mounting system 270 similar to film mounting system 104 of FIG. 7, seals the bottom side of cell 272 formed by body 264. Cell 272 is gas- or liquid-sealed by cap 266 and film strip 268 in accordance with the type of sample that is to be injected into the cell. Cap 266 includes a centrally mounted, upwardly extending cylindrical stem 274 surmounted by a cylindrical disk 276; stem 274 and disk 276 are analogous to stem 103 and disk 105 of FIG. 7.

In accordance with the present invention, cap 266 forms a vertical, cylindrical passage 278 that opens at the top disk 276, extends through stem 274 and top wall 267, and opens at the bottom of top wall 267 into cell 272. A circular septum 280 surmounts disk 276 and seals top opening 282 of passage 278. A cylindrical septum extension 284 that extends downwardly from septum 280 into passage 278 aids in sealing top opening 282. Septum 280 is held into position at the top of disk 276 by a clamp 286 that extends around the top, side, and under surface of disk 276 and over septum 280 at the top surface of disk 226. Clamp 280 is preferably made of a thin, malleable metal. Clamp 280 forms a circular aperture 288 that is centrally aligned with top opening 282 of passage 278. Cell 272 is sealed against the escape of a sample liquid or gas by film 268 and septum 280. Septum 280 is made of a material such as rubber that can be punctured by a needle that is self-biasable about the needle so as to keep cell 272 sealed.

FIG. 22 shows septum 280 by a hollow loading needle 290 and an optional hollow unloading needle 292. Loading and unloading needles 290 and 292 are shown as hypodermic needles. Needles 290 and 292 are connected to external adapter connectors 294 and 296 respectively that are in turn connected to syringe chambers (not shown) in a manner known in the art. Both needles 290 and 292 are preferably held in position by a mounting clip 294 positioned above disk 276. Loading needle 290 is adapted to pass a liquid or gas sample into cell 272. The tip, or outlet, 296 of loading needle 290 can be positioned in cell 272 at a distance from bottom film strip 268 in accordance with the specific weight of the sample being loaded. Likewise, tip, or inlet, 298 of unloading needle 292 is adjusted relative to outlet tip 296. Outlet tip 296, for example, will be dropped to position 296' proximate to film 268 when a lightweight gas such as helium is being injected into cell 272. For a heavy gas, inlet tip 298 of unloading needle 292 will be positioned at a low point such as at 298' for evacuation of air trapped at the bottom of cell 272. At the high inlet tip position 298 excess liquid can be purged from cell 272 during the loading operation. Upon completion of loading operation, needles 290 and 294 are withdrawn from cell 272 and septum 280 self-seals about the punctures. Unloading needle 292 can be connected to a suction source or it can be used to release fluid so as to stabilize the pressure in cell 272. Also, unloading needle 292 can be used as a purge needle during application of cap 266 to release excessive gas pressure and so avoid bowing of film strip 268.

It is to be understood that passage 278 can be formed by a stem and disk attached to a top transverse wall integral with the holder body as shown in FIG. 11.

For further information relating to septum composition, shape, support closures, and techniques, please refer to the following literature:

1. Catalog: GC LC MS AA, Page 44—SEPTA; Company: Scientific Glass Engineering Inc.; Copyright: SGE 1982

2. Catalog: No. 841-V, GC/LC, Auto Sampler, Vials, Caps, Seals, Pages 4 through 12; Company: Chemical Research Supplies, Division of L.C. Company, Inc.

3. Catalog: Products for Research, Laboratory Apparatus, Containers and Instrumentation, Pages 30, 31, 32, 33, 39, and 123; Company: Wheaton Scientific; Copyright: 1984.

The embodiments of the invention particularly disclosed here are presented merely as examples of the invention. Other embodiments, forms and modifications of the invention coming within the proper scope of the appended claims will, of course, readily suggest themselves to those skilled in the art.

What is claimed is:

1. A sample holder for liquid or powder sample material for X-ray spectroscopic analysis, comprising, in combination:
   a body having an outer wall and a transverse wall having an outside surface, said transverse wall being secured to said outer wall, said outer wall and said transverse wall defining a cell adapted to contain said sample material, said outer wall including a rim portion defining an open face of said body and of said cell,
   handling support means extending substantially perpendicularly outwardly from the center portion of said outside surface of said transverse wall, said handling support means being for providing a grip for a tool used in the process of raising or lowering said sample holder, said handling support means being equally accessible to said tool completely around said handling support means, and
   film means for maintaining a taut flat film surface for said sample material for X-ray analysis across said open face of said cell and for sealing said open face of said cell, said film means including means for securing said film means to said outer wall of said body.

2. A sample holder according to claim 1, wherein said handling support means includes a stem member extending substantially perpendicularly outwardly from the center portion of said outside surface of said transverse wall and a top member affixed to the end of said stem member.

3. A sample holder according to claim 2, wherein said outer wall is substantially cylindrical and said cell is substantially cylindrical, said outside surface of said transverse wall is substantially circular and said stem member is substantially cylindrical and is axially aligned with said circular outside surface.

4. A sample holder according to claim 3, wherein said top member is a substantially cylindrical disk member affixed to and axially aligned with said stem member, said disk member having a diameter greater than the diameter of said stem member and less than the diameter of said circular outside surface.

5. A sample holder according to claim 4, further including a cover member removably secured to said outer wall of said body, said cover member including said transverse wall.

6. A sample holder according to claim 5, wherein said disk member and said stem member form a central passage having a top opening at the top surface of said disk member and a bottom opening to said cell.

7. A sample holder according to claim 6, further including septum means positioned across said top surface of said disk member, said septum means being for sealing said top opening to said passage, said septum means further being capable of being punctured by a hollow loading needle and of maintaining the seal of said top opening; and affixing means for holding said septum means to said disk member.

8. A sample holder according to claim 7, wherein said loading needle is capable of passing fluid sample material to said cell and said film means and said septum means are capable of maintaining a sealed cell for holding said fluid sample after loading into said cell.

9. A sample holder according to claim 7, wherein said septum means is further capable of being punctured by a hollow unloading needle and of subsequently maintaining said seal across said top opening.

10. A sample holder according to claim 9, wherein said fluid sample material is a liquid.

11. A sample holder according to claim 9, wherein said fluid sample material is a gas.

12. A sample holder according to claim 9, wherein said septum means is further capable of maintaining a seal across said top opening after said loading and unloading needles have been withdrawn from said cell after loading said fluid with said cell.

13. A sample holder according to claim 9, wherein said loading and unloading needles are capable of being slidably adjusted in said cell through said septum means so as to pass fluid from said cell through said unloading needle so as to maintain a pressure balance in said cell during fluid sample material loading operation.

14. A sample holder according to claim 5, wherein said transverse wall has a vent means for passing gas between said cell and the outside of said body.

15. A sample holder according to claim 14, wherein said vent means includes baffle means for inhibiting the passage of liquid or powdered sample material from said cell.

16. A sample holder according to claim 15, wherein said outer wall includes another rim portion opposed to said rim portion forming another open face opposed to said open face, said transverse wall being spaced from said second open face, said transverse wall further defining a well having said another open face of said body, said stem member and said top member means being positioned in said well, said well being adapted to contain sample material that exudes from said cell through said baffled vent means, and wherein said film means includes a single layer of film.

17. A sample holder according to claim 16, further including an absorbent material containing a liquid material disposed at the center of said open face, and wherein said film means includes inner and outer film layers sandwiching said liquid sample material.

18. A sample holder according to claim 17, further including a cap member that includes said transverse wall, and mounting means associated with the periphery of said transverse wall and said outer wall for removably securing said cap member with said body with sufficient strength to hold said body to said cap when said sample holder is being lifted with said tool at said handling support means.

19. A sample holder according to claim 18, wherein said transverse wall and said outer wall form a well opposite said cell, and further including baffled vent means associated with said transverse wall for passing gas between said cell and said wall and for inhibiting the passage of liquid or powdered sample material from said cell when said sample holder is in a vacuum environment, said stem member and said disk member being positioned within said well, and wherein said film means includes a single layer of film.

20. A sample holder according to claim 19, further including an absorbent material containing a liquid sample material disposed at the center of said open face, and wherein said film means includes inner and outer film layers sandwiching said liquid sample material.

* * * * *